United States Patent
Drew et al.

(10) Patent No.: US 9,714,204 B1
(45) Date of Patent: Jul. 25, 2017

(54) PROCESS FOR PURIFYING ETHYLENE PRODUCED FROM A METHANOL-TO-OLEFINS FACILITY

(71) Applicant: Chevron Phillips Chemical Company LP, The Woodlands, TX (US)

(72) Inventors: Jennifer F. Drew, Humble, TX (US); Christina M. Barry, Houston, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 0 days.

(21) Appl. No.: 15/222,086

(22) Filed: Jul. 28, 2016

(51) Int. Cl.
| | |
|---|---|
| C07C 7/00 | (2006.01) |
| C07C 7/163 | (2006.01) |
| C10J 3/72 | (2006.01) |
| C07C 1/20 | (2006.01) |
| C07C 7/12 | (2006.01) |
| C07C 7/13 | (2006.01) |
| C07C 29/151 | (2006.01) |
| C08F 10/02 | (2006.01) |

(52) U.S. Cl.
CPC .............. *C07C 7/163* (2013.01); *C07C 1/20* (2013.01); *C07C 7/12* (2013.01); *C07C 7/13* (2013.01); *C07C 29/1518* (2013.01); *C08F 10/02* (2013.01); *C10J 3/72* (2013.01); *C10J 2300/093* (2013.01); *C10J 2300/1659* (2013.01); *C10J 2300/1665* (2013.01)

(58) Field of Classification Search
CPC . C07C 7/14841; C07C 7/14833; C07C 7/148; C07C 7/00; C07C 11/04; C07B 63/00
See application file for complete search history.

(56) References Cited

U.S. PATENT DOCUMENTS

| | | |
|---|---|---|
| 2,970,177 A | 1/1961 | Cobb, Jr. |
| 3,248,179 A | 4/1966 | Norwood |

(Continued)

FOREIGN PATENT DOCUMENTS

| | | |
|---|---|---|
| EP | 0448698 B1 | 3/1993 |
| EP | 0863922 B1 | 9/2004 |

(Continued)

OTHER PUBLICATIONS

Funk, Gregory A., et al., "A different game plan," Hyrocarbon Engineering, Dec. 2013, 4 pages.

(Continued)

*Primary Examiner* — Rip A Lee
(74) *Attorney, Agent, or Firm* — Conley Rose, P.C.; Rodney B. Carroll; Monte Rhodes

(57) ABSTRACT

Described herein are processes and systems for purifying an olefin stream which has at least 99 mol % ethylene, involving use of a sulfur guard bed to yield an effluent from the olefin stream which is substantially free of sulfur; a hydrogenation catalyst to yield an effluent from the sulfur guard bed effluent which is substantially free of sulfur, oxygen, acetylene, methyl acetylene, and propadiene; a copper-metal containing catalyst bed to yield an effluent from the hydrogenation catalyst effluent which is substantially free of sulfur, oxygen, acetylene, methyl acetylene, propadiene, carbon monoxide, and hydrogen; and a desiccant to yield a purified ethylene stream having greater than or equal to 99.875 mol % ethylene.

24 Claims, 3 Drawing Sheets

(56) References Cited

U.S. PATENT DOCUMENTS

| | | | |
|---|---|---|---|
| 3,695,002 A * | 10/1972 | Rottmayr | C07C 7/005 95/167 |
| 3,874,116 A | 4/1975 | White | |
| 3,920,717 A | 11/1975 | Marion | |
| 4,105,588 A * | 8/1978 | Balducci | B01J 20/00 502/243 |
| 4,203,823 A | 5/1980 | Carr et al. | |
| 4,499,327 A | 2/1985 | Kaiser | |
| 4,542,252 A | 9/1985 | Graziani et al. | |
| 5,414,170 A | 5/1995 | McCue et al. | |
| 5,565,175 A | 10/1996 | Hottovy et al. | |
| 5,575,979 A | 11/1996 | Hanson | |
| 5,811,621 A * | 9/1998 | van Dijk | B01D 3/009 203/73 |
| 6,239,235 B1 | 5/2001 | Hottovy et al. | |
| 6,613,951 B1 | 9/2003 | Brown et al. | |
| 7,030,284 B2 | 4/2006 | Shutt | |
| 7,166,757 B2 | 1/2007 | Fung et al. | |
| 7,357,902 B2 * | 4/2008 | Hague | C07C 7/14841 423/219 |
| 8,309,776 B2 * | 11/2012 | van Egmond | C07C 5/09 585/261 |
| 8,399,728 B2 | 3/2013 | De Haan et al. | |
| 8,426,660 B2 | 4/2013 | Sun et al. | |
| 8,431,094 B2 * | 4/2013 | Wegerer | C07C 7/005 422/600 |
| 8,674,157 B2 | 3/2014 | Dath et al. | |
| 9,238,698 B2 | 1/2016 | Kufeld et al. | |
| 2005/0033104 A1 * | 2/2005 | van Egmond | C07C 7/11 585/800 |
| 2006/0135828 A1 | 6/2006 | Shutt | |
| 2010/0048972 A1 * | 2/2010 | Sun | C07C 7/167 585/820 |
| 2012/0294774 A1 | 11/2012 | Wegerer et al. | |
| 2016/0136630 A1 | 5/2016 | Cheung et al. | |

FOREIGN PATENT DOCUMENTS

| | | |
|---|---|---|
| EP | 2736862 B1 | 10/2015 |
| WO | 2013014003 A1 | 1/2013 |

OTHER PUBLICATIONS

"How is Methanol Made?" http://www.methanol.org/methanol-basics/overview/how-is-methanol-made-.aspx, 2011, 1 page, Methanol Institute.

"Methanol to Olefins: A Pillar of Capacity Additions in China, but Does MTO have a Role in India?" IOCL Conclave, Feb. 7, 2014, 25 pages, UOP LLC.

Total Petrochemicals press release entitled "Total confirms successful operation of its Methanol-To-Olefins demonstration program—Samples of propylene made from methanol polymerized successfully into polypropylene," http://www.totalrefiningchemicals.com/SiteCollectionDocuments/Press_releases_news/2010/cp_mto-20100630-en.pdf, 2010, 2 pages.

UOP Method 578-02, "Automated Pore Volume and Pore Size Distribution of Porous Substances by Mercury Porosimetry," 1984, pp. 1-14, UOP LLC.

Wang, Wei, et al., "Mechanistic investigations of the methanol-to-olefin (MTO) process on acidic zeolite catalysts by in situ solid-state NMR spectroscopy," Catalysis Today, 2006, pp. 102-114, vol. 113, Elsevier B.V.

Wikipedia download of "UOP LLC," https://en.wikipedia.org/wiki/UPO_LLC, last modified on Jul. 25, 2016, 4 pages, Wikimedia Foundation, Inc.

* cited by examiner

PROCESS FOR PURIFYING ETHYLENE PRODUCED FROM A METHANOL-TO-OLEFINS FACILITY

TECHNICAL FIELD

This disclosure relates to the purification of ethylene produced from a methanol-to-olefins process to produce polyethylene grade ethylene.

BACKGROUND

Methanol-to-olefins (MTO) processes can produce olefin-containing streams which contain ethylene and trace levels of contaminants. The olefin-containing streams obtained from MTO processes can contain olefins other than ethylene, and the contaminants can include sulfur-containing compounds, diolefins, hydrogen, carbon monoxide, and paraffins. These other olefins and/or contaminants can prevent direct use of the olefin-containing streams in polyethylene polymerization processes without purification of the ethylene in the olefin-containing streams, since the desired olefin to be polymerized is ethylene and the contaminants can poison the catalysts used in ethylene polymerization. The olefin-containing streams obtained from MTO processes can also contain polar contaminants such as oxygenated hydrocarbons (ethers, esters, acids, carbonyls) which can deactivate certain polyethylene polymerization catalysts (e.g., Ziegler-Natta and metallocene catalysts). There is an ongoing need for purification techniques which convert olefin-containing streams obtained from MTO processes to streams suitable for feeding to ethylene polymerization processes.

SUMMARY

Disclosed herein is a process for purifying an olefin stream comprising at least 99 mol % ethylene, wherein the process comprises the steps of (a) passing the olefin stream comprising 99 mol % ethylene through a sulfur guard bed to remove substantially all sulfur compounds so as to yield a substantially sulfur-free effluent, (b) contacting the substantially sulfur-free effluent from (a) with a hydrogenation catalyst to yield an effluent substantially free of sulfur, oxygen, acetylene, methyl acetylene, and propadiene, (c) passing the effluent that is substantially free of sulfur, oxygen, acetylene, methyl acetylene, and propadiene from (b) through a copper-metal containing catalyst bed to remove carbon monoxide and hydrogen and to yield an effluent that is substantially free of sulfur, oxygen, acetylene, methyl acetylene, propadiene, carbon monoxide, and hydrogen, and (d) passing the effluent that is substantially free of sulfur, oxygen, acetylene, methyl acetylene, propadiene, carbon monoxide, and hydrogen, from (c) through a desiccant comprising alumina, molecular sieve, or a hybrid alumina-zeolite composite to remove polar contaminants and yield a purified ethylene stream comprising greater than or equal to 99.875 mol % ethylene.

Further disclosed herein is a system for purifying an olefin stream comprising at least 99 mol % ethylene, wherein the system comprises a sulfur guard bed configured to remove sulfur compounds from the olefin stream to yield a substantially sulfur-free effluent, an acetylene/oxygen converter configured to contact the substantially sulfur-free effluent with a hydrogenation catalyst to yield an effluent that is substantially free of sulfur, oxygen, acetylene, methyl acetylene, and propadiene, a copper-metal containing catalyst bed configured to remove carbon monoxide and hydrogen from the effluent that is substantially free of sulfur, oxygen, acetylene, methyl acetylene, and propadiene, to yield an effluent that is substantially free from sulfur, oxygen, acetylene, methyl acetylene, propadiene, carbon monoxide, and hydrogen, and a polisher configured to remove polar contaminants from the effluent that is substantially free of sulfur, oxygen, acetylene, methyl acetylene, propadiene, carbon monoxide, and hydrogen to yield a purified ethylene stream comprising 99.875 mol % or more ethylene, equal to or less than 1 ppm (mol) of acetylene, equal to or less than 5 ppm (mol) hydrogen, equal to or less than 1 ppm (mol) carbon monoxide, equal to or less than 1 ppm (mol) water, and equal to or less than 1 ppm (mol) total sulfur.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
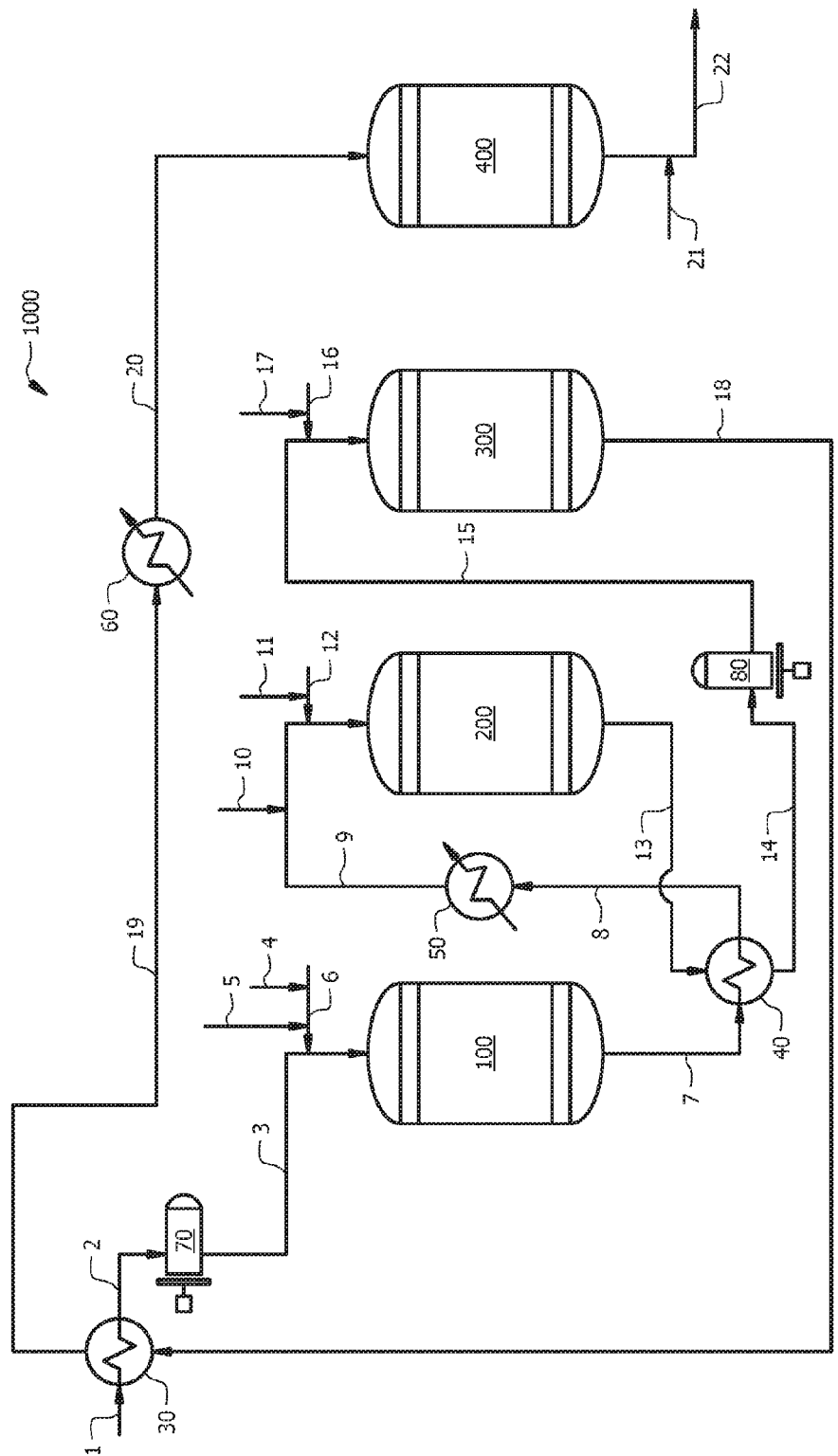
FIG. 1 illustrates a system for purifying ethylene in which one or more of the disclosed processes are performed.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

The figures described above and the written description of specific structures and functions below are not presented to limit the scope of what Applicants have invented or the scope of the appended claims. Rather, the figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the figures and are not intended to limit the scope of the invention or the appended claims.

Systems and processes for the purification of a stream produced from a methanol-to-olefins (MTO) process are disclosed herein, including a series of treatments in a specific order to remove contaminants that are problematic for downstream polyethylene polymerization processes. Particularly, the olefin stream can be treated sequentially using a sulfur-guard bed containing a catalyst or a desiccant, then a hydrogenation catalyst, then a copper-metal containing catalyst bed, and finally, a polisher which contains a desiccant. The particular order of treatment described herein enables purification of the MTO stream to yield a purified ethylene stream having polyethylene grade ethylene which is suitable for use in polyethylene production processes. The systems and processes also provide flexibility of sulfur guard bed configuration for olefin streams having different sulfur compounds, as shown and discussed in FIG. 1 and FIG. 2, as well as Example 1 and Example 2.

Turning now to the figures, FIG. 1 illustrates a system 1000 for purifying ethylene in which the disclosed processes are performed. System 1000 can include a sulfur-guard bed 100, an acetylene/oxygen converter 200, a copper-metal containing catalyst bed 300, and a polisher 400. System 1000 further can include a first heat exchanger 30, a second heat exchanger 40, a third heat exchanger 50, a fourth heat exchanger 60, an ethylene feed trim heater 70, and a copper-metal bed preheater 80. Streams 1-22 can be included in system 1000 and are described in more detail below. Within the scope of the system 1000 of FIG. 1, it is contemplated that various equipment associated with separation systems (e.g., valves, pumps, accumulators, piping, reboilers, condensers, heaters, compressors, control systems, safety equipment, and the like), while not shown for purposes of clarity, can be included in system 1000 according to techniques known in the art with the aid of this disclosure.

An olefin stream 1 containing ethylene and contaminants can be received directly or indirectly from a MTO process (not shown). The olefin stream 1 can comprise at least 99 mol % ethylene. The remainder of the olefin stream 1 can comprise less than 1 mol % of other components such as one or more of the contaminants described herein (e.g., sulfur compounds, acetylene, methyl acetylene, propadiene, oxygen, hydrogen, carbon monoxide, alcohols, carbonyls, carbon dioxide, water, phosphine, arsine, nitrous oxide, ammonia). In aspects where the MTO process cannot provide an olefin stream 1 having at least 99 mol % ethylene, a recovery system can be utilized between the MTO process and system 1000 such that olefin stream 1 having at least 99 mol % ethylene is obtained (e.g., the olefin stream 1 is obtained indirectly from the MTO process).

System 1000 is particularly configured for olefin stream 1 which contains sulfur compounds of hydrogen sulfide ($H_2S$), carbonyl sulfide (COS), mercaptans, dimethyl sulfide (DMS), and dimethyl disulfide (DMDS). The composition of olefin stream 1 may include at least 99 mol % ethylene, 1-10 ppm (mol) sulfur compounds, 1-30 ppm (mol) acetylene, 1-30 ppm (mol) methyl acetylene, 1-30 ppm (mol) propadiene, 1-10 ppm (mol) oxygen, 1-20 ppm (mol) hydrogen, 1-10 ppm (mol) carbon monoxide, 1-30 ppm (mol) polar contaminants (total concentration of water, alcohols, and carbonyl compounds), and 1-20 ppm (mol) carbon dioxide.

Other nonlimiting concentrations of contaminants in the olefin stream 1 are presented in Example 1 and Example 2 below and include inerts (0.125 mol %), propylene (20 ppm (mol)), phosphine (0.1 ppm (mol)), arsine (0.1 ppm (mol)), nitrous oxide (1 ppm (mol)), and ammonia (1 ppm (mol)).

Olefin stream 1 can flow to a first heat exchanger 30 where olefin stream 1 can be heated (where heat is transferred) by exchanging thermal energy with a heating medium (e.g., steam or the contents of stream 18) to yield stream 2. When olefin stream 1 exchanges thermal energy with the contents of stream 18, the first heat exchanger 30 can be a cross flow heat exchanger. Heated stream 2 comprising the heated contents of olefin stream 1 flows from the first heat exchanger 30 to an ethylene feed trim heater 70. The ethylene feed trim heater 70 can be used for heat input during start-up. Stream 3 comprising the further heated contents at a temperature effective for the subsequent removal of contaminants in the sulfur guard bed 100 (e.g., at a temperature of from about 200° F. (93.3° C.) to about 350° F. (176.7° C.)) can flow from the trim heater 70 to the sulfur guard bed 100.

The sulfur guard bed 100 can be configured to remove sulfur compounds from ethylene and other components received in stream 3 to yield a substantially sulfur-free effluent in streams 7 and 8. The disclosure contemplates that stream 1 or 2 can alternatively feed to the sulfur guard bed 100 (e.g., heat exchanger 30 and/or ethylene feed trim heater 70 are not used).

In FIG. 1, the sulfur guard bed 100 can be a bed of nickel catalyst contained in a vessel. The nickel catalyst can comprise nickel deposited on a support material. The nickel can be in the form of metallic nickel, nickel oxide, or both metallic nickel and nickel oxide. The support material can be silica, silico-alumina, alumina, kieselguhr, zeolites, other similar materials, whether amorphous or crystalline, or a combination thereof. Metallic nickel can be present in the nickel catalyst in an amount of 1 wt. % to 50 wt. % based on a total weight of the nickel catalyst. The total weight of metallic nickel and/or nickel oxide can be present in an amount of about 90 wt. % based on a total weight of the nickel catalyst. Preferably, the weight ratio of metallic nickel to nickel oxide is from 0.1 to 10. The support material can be present in an amount of from 10 to 95 wt. % based on a total weight of the nickel catalyst. The sulfur guard bed 100 can include any number of beds in any configuration known in the art with the aid of this disclosure.

The contents received by the sulfur guard bed 100 can pass over the nickel catalyst at a temperature of from about 200° F. (93.3° C.) to about 350° F. (176.7° C.).

Stream 4 can be used to provide hydrogen into the sulfur guard bed 100 for initial bed reduction prior to contact with the contents of olefin stream 1 received via one of streams 1, 2, or 3. Stream 5 can be used to provide air for oxidation of the nickel catalyst prior to bed removal. Generally, the sulfur guard bed 100 of system 1000 can be non-regenerable, and sulfur guard bed 100 can be a pair of nickel catalyst beds which are alternated so that a spent bed of the pair of beds can be removed and replaced while a fresh bed of the pair of beds can keep the system 1000 online. Stream 6 can be used to provide nitrogen to the sulfur guard bed 100. Nitrogen can be used as the carrier gas for hydrogen flowing into stream 6 from stream 4 and/or a carrier gas for the oxygen flowing into stream 6 from stream 5.

A sulfur guard bed effluent which is substantially free of sulfur can flow from the sulfur guard bed 100 in stream 7. The terms "substantially sulfur-free" and "substantially free of sulfur" can be used interchangeably, and as used herein, refer to a concentration of sulfur compounds which is equal to or less than about 1 ppm (mol) based on the total moles in a stream. The term "substantially sulfur-free effluent" refers to an effluent stream exiting a reactor or vessel, catalyst bed, guard bed, polisher, or desiccant bed and having a total concentration of sulfur compounds equal to or less than about 1 ppm (mol) based on the total moles in the effluent. Thus, the substantially sulfur-free effluent flowing in stream 7 can have equal to or less than about 1 ppm (mol) sulfur compounds based on the total moles of components flowing in stream 7. The level of sulfur compounds in stream 7 generally can be maintained for all streams downstream of the sulfur guard bed 100 in system 1000. The substantially sulfur-free effluent in stream 7 can have a temperature of about 200° F. (93.3° C.) to about 400° F. (204.4° C.).

The substantially sulfur-free effluent in stream 7 can flow to the second heat exchanger 40 where the contents of stream 7 can be cooled (where heat is transferred) by exchanging thermal energy with a cooling medium (e.g., refrigerant or the contents of stream 13) to yield stream 8. The cooled contents in cooled stream 8 can have a temperature lower than stream 7 and higher than stream 9. When stream 7 exchanges thermal energy with the contents of stream 13, the second heat exchanger 40 can be a cross flow heat exchanger. Cooled stream 8, comprising the cooled contents of stream 7, can flow from the second heat exchanger 40 to a third heat exchanger 50 for further cooling. Stream 9, comprising the further cooled contents of stream 8, can flow from the third heat exchanger 50 to the acetylene/oxygen converter 200. The temperature of stream 9 can be a temperature effective for the subsequent removal of contaminants in the acetylene/oxygen converter 200 (e.g., a temperature of about 200° F. (93.3° C.) to about 300° F. (148.9° C.)).

Stream 10 can be used to provide hydrogen to the acetylene/oxygen converter 200 during operation thereof. Additionally, stream 10 can be used to activate the catalyst in the acetylene/oxygen converter 200. While stream 10 is shown as providing hydrogen via stream 9 in FIG. 1, it is contemplated that hydrogen can be provided directly to the acetylene/oxygen converter 200 or at any point upstream of the acetylene/oxygen converter 200 (e.g., streams 1, 2, 3, 4, 5, 6, 11, or 12; into the substantially sulfur-free effluent of the sulfur guard bed in stream 7, 8, or 9; or into the sulfur guard bed 100). Stream 11 can be used to provide air for oxidation of the hydrogenation catalyst in the acetylene/oxygen converter 200 prior to removal of the catalyst. Stream 12 can be used to provide nitrogen to the acetylene/oxygen converter 200. Nitrogen can be a carrier gas for the hydrogen during operation of the acetylene/oxygen converter 200 and a carrier gas for oxygen during oxidation of the hydrogenation catalyst.

The acetylene/oxygen converter 200 can be configured to contact the substantially sulfur-free effluent received via stream 9 with a hydrogenation catalyst to yield effluent stream 13 that can be substantially free of sulfur, oxygen, acetylene, methyl acetylene, and propadiene. In the alternative, it is contemplated that the substantially sulfur-free effluent can be received by the acetylene/oxygen converter 200 via stream 7 or 8, and stream 7 or 8 can be contacted with the hydrogenation catalyst to yield effluent stream 13 which is substantially free of sulfur, oxygen, acetylene, methyl acetylene, and propadiene. Stream 13 can be referred to herein as the acetylene/oxygen converter effluent or the hydrogenation catalyst effluent.

In the acetylene/oxygen converter 200, acetylene, methyl acetylene, propadiene, or a combination thereof can be converted to olefins; and oxygen can be converted to water. Water is considered a polar contaminant within the scope of this disclosure. Thus, not only can the olefin stream 1 contain polar contaminants from the MTO process, the polar contaminants (e.g., water) can be generated by the components of system 1000, which necessitates removal of the polar contaminants in a system component(s) (e.g., polisher 400) downstream of the component(s) (e.g., the acetylene/oxygen converter 200 and the copper-metal containing catalyst bed 300) which generate the polar contaminants.

The contents received by the acetylene/oxygen converter 200 are contacted with the hydrogenation catalyst at a temperature of about 200° F. (93.3° C.).

The hydrogenation catalyst can be configured in one or more bed configurations known in the art with the aid of this disclosure, e.g., referred to as one or more hydrogenation catalyst beds herein. The hydrogenation catalyst can comprise an inorganic support and palladium. The hydrogenation catalyst can further comprise an organophosphorus compound (for example impregnated in or on the inorganic support thereof). Additionally or alternatively, the hydrogenation catalyst can comprise copper in a reduced state.

The inorganic support can comprise aluminas, silicas, titanias, zirconias, aluminosilicates (for example clays, ceramics, zeolites, or combinations thereof), spinels (for example zinc aluminate, zinc titanate, magnesium aluminate, or combinations thereof), or combinations thereof. The support can be an alumina support such as an alpha ($\alpha$)-alumina support or a chlorided alpha alumina support.

The inorganic support can have a surface area of from about 2 to about 100 square meters per gram ($m^2/g$); alternatively, from about 2 $m^2/g$ to about 75 $m^2/g$; alternatively, from about 3 $m^2/g$ to about 50 $m^2/g$; alternatively, from about 4 $m^2/g$ to about 25 $m^2/g$; alternatively, from about 5 $m^2/g$ to about 15 $m^2/g$; alternatively, from about 5 $m^2/g$ to about 10 $m^2/g$. The surface area of the support can be determined using any suitable method. An example of a suitable method includes the Brunauer, Emmett, and Teller ("BET") method, which measures the quantity of nitrogen adsorbed on the support. Alternatively, the surface area of the support can be measured by a mercury intrusion method such as is described in ASTM UOP 578-02, entitled "Automated Pore Volume and Pore Size Distribution of Porous Substances by MERCURY Porosimetry," which is incorporated herein by reference in its entirety.

Particles of the inorganic support generally have an average diameter of from about 1 mm to about 10 mm; alternatively, from about 1 mm to about 6 mm; alternatively, from about 2 mm to about 6 mm; alternatively, from about 3 mm to about 5 mm. The inorganic support can have any suitable shape, including round or spherical (for example spheres, ellipsoidal, or combinations thereof), pellets, cylinders, granules (for example regular, irregular, or combinations thereof), extrudates (trilobe, quadrilobe, rings, wagonwheel, monoliths, or combinations thereof). Methods for shaping particles include, for example, extrusion, spray drying, pelletizing, marumerizing, agglomeration, oil drop, and the like. The shape of the inorganic support can be cylindrical; alternatively, the shape of the inorganic support can be spherical. Alternatively, the shape of the inorganic support can be an extrudate.

The inorganic support can be present in an amount such that it can comprise the balance of the hydrogenation catalyst when all other components are accounted for.

The hydrogenation catalyst can comprise palladium. The palladium can be added to the inorganic support by contacting the inorganic support with a palladium-containing compound to form a palladium supported catalyst as will be described in more detail later herein. Examples of suitable palladium-containing compounds include without limitation palladium chloride, palladium nitrate, ammonium hexachloropalladate, ammonium tetrachloropalladate, palladium acetate, palladium bromide, palladium iodide, tetraamminepalladium nitrate, or combinations thereof. The palladium-containing compound can be a component of an aqueous solution. Additionally or alternatively, the palladium-containing compound can be a component of an acidic solution, for example an aqueous solution comprising a mineral acid. An example of palladium-containing solution suitable for use in this disclosure includes without limitation a solution comprising palladium metal.

The hydrogenation catalyst can be prepared using a palladium-containing compound in an amount of from about 0.005 wt. % to about 5 wt. % based on the total weight of the hydrogenation catalyst; alternatively, from about 0.01 wt. % to about 3 wt. %; alternatively, from about 0.02 wt. % to about 1 wt. %; alternatively, from about 0.02 wt. % to about 0.5 wt. %; alternatively, from about 0.02 wt. % to about 0.1 wt. %; alternatively, from about 0.02 wt. % to about 0.04 wt. %. The amount of palladium incorporated into the hydrogenation catalyst can be in the range described herein for the amount of palladium-containing compound used to prepare the hydrogenation catalyst.

The hydrogenation catalyst can further comprise an organophosphorus compound. The organophosphorus compound can be represented by the general formula of $(R)_x(OR')_yP=O$; wherein x and y are integers ranging from 0 to 3 and x plus y equals 3; wherein each R can be hydrogen, a hydrocarbyl group, or combinations thereof; and wherein each R' is, when present, a hydrocarbyl group. The organophosphorus compound can include compounds such as phosphine oxides, phosphinates, phosphonates, phosphates, or combinations of any of the foregoing. For purposes of this application, the term "hydrocarbyl(s)" or "hydrocarbyl group(s)" is used herein in accordance with the definition adopted by the International Union of Pure and Applied Chemistry (IUPAC): as a univalent group or groups derived by the removal of one hydrogen atom from a carbon atom of a "hydrocarbon." A hydrocarbyl group can be an aliphatic hydrocarbon, inclusive of acyclic and cyclic groups. A hydrocarbyl group can include rings, ring systems, aromatic rings, and aromatic ring systems. Hydrocarbyl groups can include, by way of example, aryl, alkyl, cycloalkyl, and combinations of these groups, among others. Hydrocarbyl groups can be linear or branched unless otherwise specified. For the purposes of this application, the terms "alkyl," or "cycloalkyl" refers to a univalent group derived by removal of a hydrogen atom from any carbon atom of an alkane. For the purposes of this application, the terms "aryl," or "arylene" refers to a univalent group derived by removal of a hydrogen atom from any carbon atom of an aryl ring.

As described above, the effluent of the acetylene/oxygen converter 200, which can flow in stream 13, can be substantially free of sulfur, oxygen, acetylene, methyl acetylene, and propadiene. "Substantially free of sulfur, oxygen, acetylene, methyl acetylene, and propadiene" and "substantially sulfur-, oxygen-, acetylene-, methyl acetylene-, and propadiene-free" can be used interchangeably, and as used herein, refer to a concentration of sulfur compounds which is equal to or less than about 1 ppm (mol) based on the total moles in the stream; a concentration of oxygen which is equal to or less than 1 ppm (mol) based on the total moles in the stream; a concentration of acetylene equal to or less than about 1 ppm (mol) based on the total moles in the stream; a concentration of methyl acetylene which is equal to or less than 1 ppm (mol) based on the total moles in the stream, and a concentration of propadiene equal to or less than 1 ppm (mol) based on the total moles in the stream. Thus, the effluent flowing in stream 13 which is substantially free of sulfur, oxygen, acetylene, methyl acetylene, and propadiene, has equal to or less than about 1 ppm (mol) of sulfur compounds, equal to or less than 1 ppm (mol) oxygen, equal to or less than about 1 ppm (mol) of acetylene, equal to or less than 1 ppm (mol) methyl acetylene, and equal to or less than 1 ppm (mol) propadiene based on the total moles of components flowing in the stream 13.

The temperature of stream 13 can be about 200° F. (93.3° C.) to 300° F. (148.9° C.). Stream 13 can flow to a heat exchanger (e.g., second heat exchanger 40 in FIG. 1) where the contents of stream 13 are heated (where heat is transferred) by exchanging thermal energy with a heating medium (e.g., steam or contents of stream 7 as shown in FIG. 1). When exchanging thermal energy with the contents of stream 7 as shown in FIG. 1, the second heat exchanger 40 can be a cross flow heat exchanger. The temperature of the heated components in stream 14 can be higher than a temperature of stream 13 and lower than the temperature of stream 15. Heated components flow in stream 14 to a preheater 80, and the preheated components flow to the copper-metal containing catalyst bed 300 in stream 15. The temperature of stream 15 is a temperature effective for the subsequent removal of contaminants in the copper-metal containing catalyst bed 300 (e.g., a temperature of about 200° F. (93.3° C.) to about 300° F. (148.9° C.)).

The copper-metal containing catalyst bed 300 is configured to remove carbon monoxide and hydrogen from the contents received from stream 15. In the alternative, it is contemplated that the copper-metal containing catalyst bed 300 can receive the effluent of the acetylene/oxygen converter 200 from stream 13 or 14.

The contents received by the copper-metal containing catalyst bed 300 are passed through a bed of copper-metal containing catalyst at a temperature of from about 200° F. (93.3° C.) to about 300° F. (148.9° C.).

The copper-metal containing catalyst bed 300 can be a copper oxide (Cu(II)O) catalyst bed configured as one or more catalyst beds in a vessel. The copper-metal containing catalyst can be copper oxide with or without a support. Suitable supports include zeolites, carbon, inorganic oxides and mixed oxides including silica, alumina, modified alumina, aluminosilicate, magnesium oxide, clay, zirconia, titania, porous glass, or a combination thereof. The copper oxide can be placed on the support using techniques such as impregnation, ion exchange, vapor deposition, mixing, dispersion, and the like. The copper-metal containing catalyst bed 300 can be arranged in a vessel in any configuration known in the art with the aid of this disclosure.

The copper-metal containing catalyst bed 300 can remove carbon monoxide and hydrogen by converting hydrogen to water and by converting carbon monoxide to carbon dioxide. Water is considered a polar contaminant within the scope of this disclosure. Thus, not only can the olefin stream 1 contain polar contaminants from the MTO process, and not only can the acetylene/oxygen converter 200 generate water by converting oxygen to water, the polar contaminants (e.g., water) can be generated by other components of system 1000 (e.g., the copper-metal containing catalyst bed 300), which necessitates removal of the polar contaminants in a system component(s) (e.g., polisher 400) downstream of the components (e.g., the acetylene/oxygen converter 200 and the copper-metal containing catalyst bed 300) which generate the polar contaminants.

The effluent of the copper-metal containing catalyst bed 300, which can flow in stream 18, can be substantially free of sulfur, oxygen, acetylene, methyl acetylene, propadiene, carbon monoxide, and hydrogen.

"Substantially free of sulfur, oxygen, acetylene, methyl acetylene, propadiene, carbon monoxide, and hydrogen" and "substantially sulfur-, oxygen-, acetylene-, methyl acetylene-, propadiene-, carbon monoxide-, and hydrogen-free" can be used interchangeably, and as used herein, refer to a concentration of sulfur compounds which is equal to or less than about 1 ppm (mol) based on the total moles in the stream; a concentration of oxygen which is equal to or less than 1 ppm (mol) based on the total moles in the stream; a concentration of acetylene which is equal to or less than about 1 ppm (mol) based on the total moles in the stream; a concentration of methyl acetylene which is equal to or less than 1 ppm (mol) based on the total moles in the stream; a concentration of propadiene which is equal to or less than 1 ppm (mol) based on the total moles in the stream; a concentration of carbon monoxide which is equal to or less than 1 ppm (mol) based on the total moles in the stream; and a concentration of hydrogen which is equal to or less than 5 ppm (mol) based on the total moles in the stream. Thus, the effluent flowing in stream 18, which can be substantially free of sulfur, oxygen, acetylene, methyl acetylene, propadiene, carbon monoxide, and hydrogen, can have equal to or less than about 1 ppm (mol) of sulfur compounds, equal to or less than 1 ppm (mol) oxygen, equal to or less than about 1 ppm (mol) of acetylene, equal to or less than 1 ppm (mol) methyl acetylene, equal to or less than 1 ppm (mol) propadiene, equal to or less than 1 ppm (mol) carbon monoxide, and equal to or less than 5 ppm (mol) hydrogen based on the total moles of components flowing in the stream 18.

The effluent in stream 18 can also be referred to herein as the copper-metal containing catalyst bed effluent herein.

The copper-metal containing catalyst bed 300 can be regenerable. Air can be provided to the copper-metal containing catalyst bed 300 via stream 17 for oxidation of the bed during regeneration thereof once saturated with contaminants. Stream 16 can provide a regenerating gas selected from nitrogen, sulfur-free methane, sulfur-free ethane, sulfur-free propane, sulfur-free butanes, noble gases, or a combination thereof to the copper-metal containing catalyst bed 300 for regeneration. Regeneration of the copper-metal containing catalyst bed 300 can be via any technique known in the art with the aid of this disclosure. The copper-metal containing catalyst bed 300 can be configured as two vessels in parallel, where a spent bed of the pair is regenerated while the fresh bed of the pair is online and in operation.

Effluent can flow from the copper-metal containing catalyst bed 300 in stream 18 at a temperature of about 200° F. (93.3° C.) to about 400° F. (204.4° C.). In FIG. 1, the effluent of the copper-metal containing catalyst bed 300 can flow in stream 18 to a heat exchanger, for example, the first heat exchanger 30. In the heat exchanger (e.g., the first heat exchanger 30), the effluent can be cooled with a cooling medium (e.g., a refrigerant or stream 1). When stream 18 is cooled using stream 1, the first each exchanger 30 can be a cross flow heat exchanger. The cooled effluent flows from the first heat exchanger 30 via stream 19 to a fourth heat exchanger 60 for further cooling with a cooling medium. The temperature of the cooled effluent in stream 19 can be lower than the contents of stream 18 and higher than the contents of stream 20. The heat exchanger 60 can be an ethylene polisher precooler. The further cooled contents flow in stream 20 to polisher 400. The temperature of the further cooled contents in stream 20 can be effective for the subsequent removal of contaminants in the polisher 400 (e.g., a temperature of less than about 100° F. (37.8° C.)).

With continued reference to FIG. 1, the polisher 400 can be configured to remove polar contaminants from stream 20 which is substantially free of sulfur, oxygen, acetylene, methyl acetylene, propadiene, carbon monoxide, and hydrogen. Alternatively, it is contemplated that the polisher 400 can receive the effluent of the copper-metal containing catalyst bed 300 via stream 18 or stream 19. The polisher 400 can remove polar contaminants to yield a purified ethylene stream 22 comprising equal to or greater than 99.875 mol % ethylene and equal to or less than about 1 ppm (mol) of sulfur compounds, equal to or less than 1 ppm (mol) oxygen, equal to or less than about 1 ppm (mol) of acetylene, equal to or less than 1 ppm (mol) methyl acetylene, equal to or less than 1 ppm (mol) propadiene, equal to or less than 1 ppm (mol) carbon monoxide, equal to or less than 5 ppm (mol) hydrogen, and equal to or less than 1 ppm (mol) water based on the total moles of components flowing in stream 22. Purified ethylene stream 22 can be a polyethylene grade ethylene stream (e.g., a feed stream to a polyethylene polymerization process). The purified ethylene in stream 22 can be referred to as the polisher effluent.

The polar contaminants removed in the polisher 400 (e.g., adsorbed by the desiccant) include water introduced in the olefin stream 1 and/or generated in one or both of the acetylene/oxygen converter 200 and the copper-metal containing catalyst bed 300. The desiccant in the polisher 400 can also remove polar contaminants including alcohols (e.g., residual methanol from the MTO process) and carbonyl compounds. Other polar contaminants removed in the polisher 400 can include ammonia and oxygenates other than those disclosed herein.

The desiccant in the polisher 400 can additionally remove light acid gases ($H_2S$), carbon dioxide ($CO_2$), and carbonyl sulfide (COS) from the stream (e.g., stream 20) which enters the polisher 400, aiding in providing purified ethylene stream 22 which meets or exceeds the specifications for polyethylene grade ethylene.

The contents received by the polisher 400 can pass through a desiccant at a temperature of less than about 100° F. (37.8° C.).

The desiccant in the polisher 400 can be configured in one or more desiccant beds in a vessel. The desiccant can be molecular sieve, activated alumina, hybrid alumina-zeolite composite, silica gel, montmorillonite clay, calcium oxide, calcium sulfate, calcium chloride, activated carbon, metal salts, phosphorus-containing desiccant compounds, or a combination thereof. The term "molecular sieve" refers to a material having a fixed, open-network structure, usually crystalline, that can be used to separate hydrocarbons from the impurities disclosed herein by selective occlusion of one or more of the impurities. An example of a molecular sieve is a zeolite, which has a silicate lattice, often in association with aluminum, boron, gallium, iron, and/or titanium. An example of a zeolite is a 13× molecular sieve. The molecular sieves can have a pore size of 10 angstroms (Å) or more. Alternatively, the pore size can be 10 angstroms (Å) or less. An example of activated alumina is sodium treated alumina.

The desiccant in the polisher 400 can be regenerable. A regenerating gas selected from nitrogen, sulfur-free methane, sulfur-free ethane, sulfur-free propane, sulfur-free butanes, noble gases, or a combination thereof can be provided to the polisher 400 via stream 21 for regeneration of the desiccant when the desiccant is saturated with polar contaminants. Regeneration of the desiccant in the polisher 400 can be via any technique known in the art with the aid of this disclosure. The polisher 400 can be configured as two vessels in parallel, where a saturated desiccant of the pair of vessels is regenerated while the fresh desiccant of the pair of vessels is online and in operation.

Figure 2:
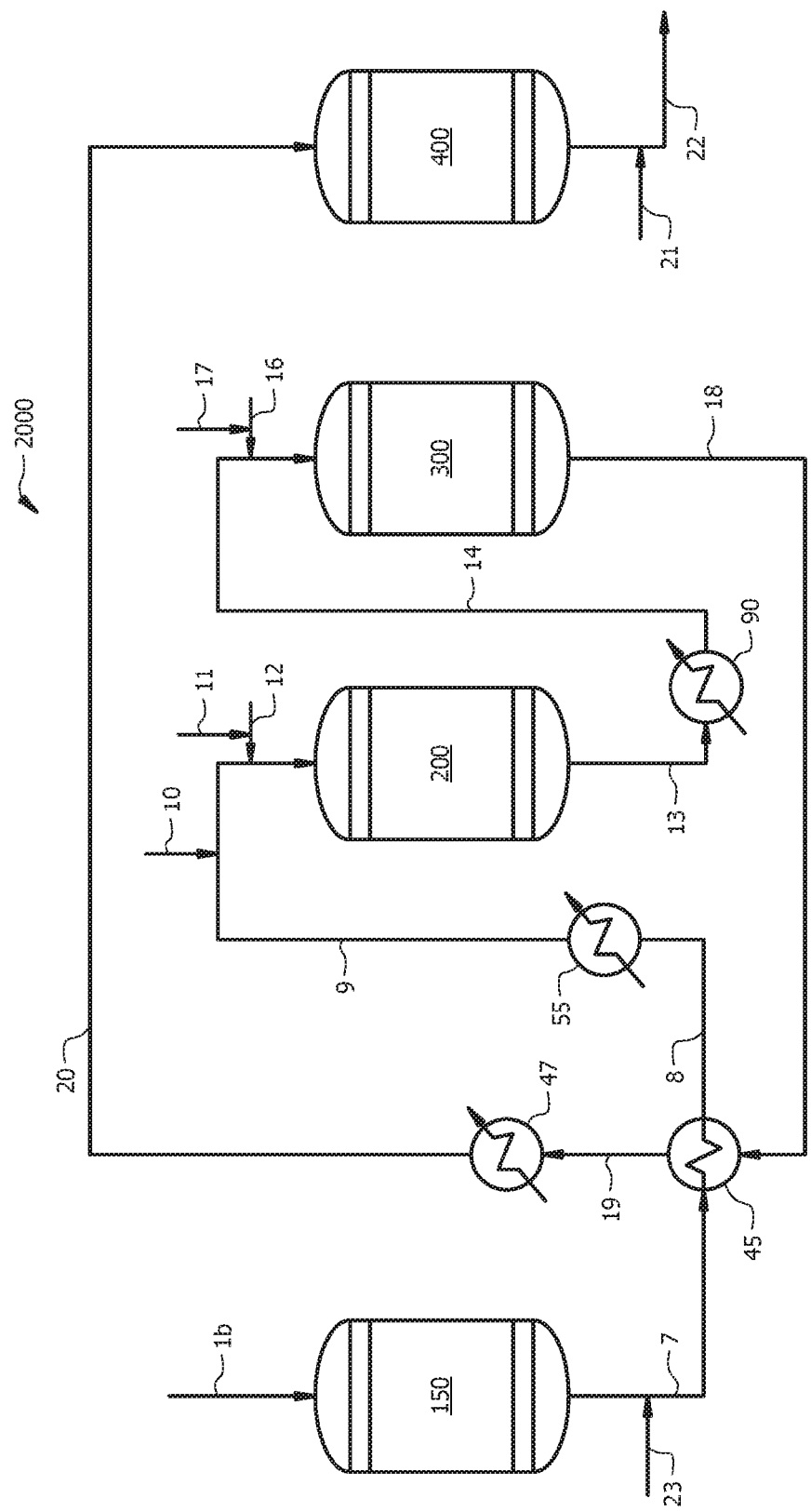
FIG. 2 illustrates another system for purifying ethylene in which one or more of the disclosed processes are performed.

FIG. 2 illustrates a system 2000 for purifying ethylene in the disclosed processes. System 2000 can include a sulfur-guard bed 150, an acetylene/oxygen converter 200, a copper-metal containing catalyst bed 300, and a polisher 400. The system 2000 can further include heat exchanger 45, heat exchanger 47, heat exchanger 55, and preheater 90. Streams 1b, 7-14, and 16-22 are included in system 2000 and are described in more detail below. Within the scope of system 2000 of FIG. 2, it is contemplated that various equipment associated with separation systems (e.g., valves, pumps, accumulators, piping, reboilers, condensers, heaters, compressors, control systems, safety equipment, and the like), while not shown for purposes of clarity, can be included in system 2000 according to techniques known in the art with the aid of this disclosure.

The olefins stream 1b in system 2000 can contain the same components as the olefin stream 1 in system 1000, except that the sulfur compounds do not include mercaptans, DMS, or DMDS (e.g., the sulfur compounds only include $H_2S$ and COS). The olefin stream 1b in system 2000 can feed directly to the sulfur guard bed 150 without heating in a heat exchanger. Thus, the temperature of the contents in stream 1b of system 2000 can be effective for the subsequent removal of contaminants in the sulfur guard bed 150 (e.g., a temperature less than about 100° F. (37.8° C.)).

The contents of stream 1b as received by the sulfur guard bed 150 can pass through a desiccant at a temperature of less than about 100° F. (37.8° C.). As the contents of stream 1b pass through the desiccant, the desiccant removes (e.g., adsorbs) hydrogen sulfide ($H_2S$) and carbonyl sulfide (COS) to yield a substantially sulfur-free effluent which has equal to or less than about 1 ppm (mol) sulfur compounds (e.g., hydrogen sulfide, carbonyl sulfide, or both) based on the total moles in the stream (e.g., stream 7) containing the substantially sulfur-free effluent. The desiccant in the sulfur guard bed 150 can also remove (e.g., adsorb) polar contaminants including water, alcohols (e.g., residual methanol from the MTO process), and carbonyl compounds, as well as carbon dioxide contained in olefin stream 1b. The substantially sulfur-free effluent thus can also contain reduced amounts of polar contaminants and carbon dioxide, for example, equal to or less than about 1 ppm (mol) water, equal to or less than about 1 ppm (mol) alcohols, equal to or less than about 1 ppm (mol) carbonyl compounds, and equal to or less than about 1 ppm (mol) carbon dioxide.

The desiccant in the sulfur guard bed 150 can be configured in one or more desiccant beds in a vessel. The desiccant can be molecular sieve, activated alumina, hybrid alumina-zeolite composite, silica gel, montmorillonite clay, calcium oxide, calcium sulfate, calcium chloride, activated carbon, metal salts, phosphorus-containing desiccant compounds, or a combination thereof. The term "molecular sieve" as used herein refers to a material having a fixed, open-network structure, usually crystalline, that can be used to separate hydrocarbons from the impurities disclosed herein by selective occlusion of one or more of the impurities. An example of a molecular sieve is a zeolite, which has a silicate lattice, often in association with aluminum, boron, gallium, iron, and/or titanium. An example of a zeolite is a 13× molecular sieve. The molecular sieves can have a pore size of 10 angstroms (Å) or more. Alternatively, the pore size can be 10 angstroms (Å) or less. An example of activated alumina is sodium treated alumina.

The desiccant in the sulfur guard bed 150 can be regenerable. Stream 23 can provide a regenerating gas selected from nitrogen, sulfur-free methane, sulfur-free ethane, sulfur-free propane, sulfur-free butanes, noble gases, or a combination thereof to the sulfur guard bed for regeneration of the desiccant when the desiccant is saturated with contaminants. Regeneration of the desiccant in the sulfur guard bed 150 can be via any technique known in the art with the aid of this disclosure. The sulfur guard bed 150 can be configured as two vessels in parallel, where a saturated desiccant of the pair of vessels can be regenerated while the fresh desiccant of the pair of vessels is online and in operation.

The temperature of the contents of stream 7 can be less than about 100° F. (37.8° C.). The contents of stream 7 can pass through heat exchanger 45, where the contents of stream 7 are heated (where heat is transferred) by exchanging thermal energy with a heating medium (e.g., steam or stream 18) to yield the heated contents in stream 8. The heated contents of stream 8 can have a temperature higher than stream 7 and lower than stream 18. When stream 7 exchanges thermal energy with contents of stream 18, the heat exchanger 45 can be a cross flow heat exchanger. Heated stream 8, comprising the heated contents of stream 7, can flow from heat exchanger 45 to heat exchanger 55 for further heating. Stream 9, comprising the further heated contents of stream 8, can flow from heat exchanger 55 to the acetylene/oxygen converter 200. The temperature of stream 9 can be a temperature effective for the subsequent removal of contaminants in the acetylene/oxygen converter 200 (e.g., a temperature of about 200° F. (93.3° C.) to about 300° F. (148.9° C.)).

In an aspect, heat exchanger 45 can perform a majority of the heating of the sulfur-free effluent from the sulfur guard bed 150. In such an aspect, heat exchanger 55 in FIG. 2 can be used to supplement heating during startup and/or operation of system 2000; alternatively, heat exchanger 55 can be used only in startup while heat exchanger 45 provides heating during operation.

Streams 10, 11, and 12 of system 2000 are the same as streams 10, 11, and 12 of system 1000.

The acetylene/oxygen converter 200 of system 2000 is the same as in system 1000, yielding effluent stream 13 which is substantially free of sulfur, oxygen, acetylene, methyl acetylene, and propadiene.

While stream 10 is shown as providing hydrogen via stream 9 in FIG. 2, it is contemplated that hydrogen can be provided directly to the acetylene/oxygen converter 200 or at any point upstream of the acetylene/oxygen converter 200 (e.g., stream 1b, 11, or 12; the sulfur guard bed effluent of stream 7, 8, or 9; or into the sulfur guard bed 150).

The temperature of stream 13 can be about 200° F. (93.3° C.) to 300° F. (148.9° C.).

The contents of stream 13 can flow to preheater 90, where the contents are heated (where heat is transferred) by exchanging thermal energy with a heating medium (e.g., steam) to yield the heated components in stream 14. The temperature of stream 14 can be a temperature effective for the subsequent removal of contaminants in the copper-metal containing catalyst bed 300 (e.g., a temperature of about 200° F. (93.3° C.) to about 300° F. (148.9° C.)).

The copper-metal containing catalyst bed 300 of system 2000 can be the same as in system 1000, yielding effluent stream 18 which is substantially free of sulfur, oxygen, acetylene, methyl acetylene, propadiene, carbon monoxide, and hydrogen.

Streams 16 and 17 in system 2000 are the same as in system 1000, except in FIG. 2 streams 16 and 17 feed to stream 14.

The effluent of the copper-metal containing catalyst bed 300 in stream 18 can flow to heat exchanger 40, where the contents can be cooled (where heat is transferred) by exchanging thermal energy with a cooling medium (e.g., refrigerant or sulfur-free effluent in stream 7) to yield the cooled contents in stream 19. When the heat exchanger 40 uses stream 7 to cool stream 18, the heat exchanger 40 can be a cross flow heat exchanger.

The cooled contents in stream 19 flow to heat exchanger 47, where the contents can be further cooled with a cooling medium to yield further cooled contents in stream 20. The heat exchanger 47 can be an ethylene polisher trim cooler.

The temperatures of streams 18, 19, and 20 in FIG. 2 can have values within the range of values disclosed for streams 18, 19, and 20 in FIG. 1, respectively.

The further cooled contents in stream 20 can flow to the polisher 400, which is the same as polisher 400 in system 1000. Purified ethylene stream 22 in system 2000 can have the same specifications as purified ethylene stream 22 in system 1000. Stream 21 in system 2000 is the same as stream 21 in system 1000. Similarly to system 1000, it is contemplated in system 2000 that the polisher 400 can alternatively receive the effluent of the copper-metal containing catalyst bed 300 via stream 18 or stream 19.

Figure 3:
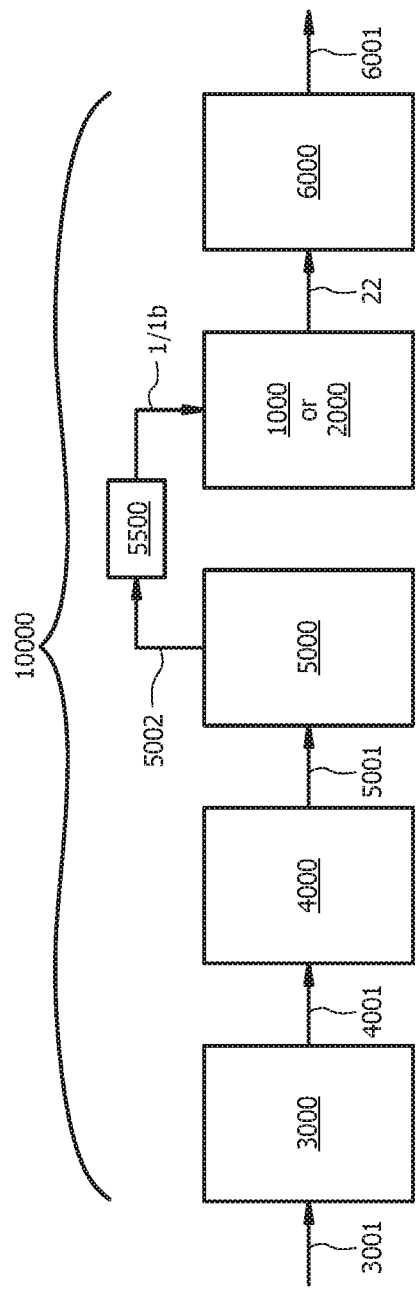
FIG. 3 illustrates a system for converting coal to polyethylene, utilizing the ethylene purification system of FIG. 1 or FIG. 2.

FIG. 3 shows a system 10000 which incorporates system 1000 or 2000 with upstream and/or downstream processes. Particularly, FIG. 3 shows a gasification system 3000 implementing a gasification process which can convert coal 3001 to a syngas stream 4001; a methanol system 4000 implementing a syngas-to-methanol process which can convert the syngas stream 4001 to a methanol stream 5001; a methanol-to-olefin (MTO) system 5000 implementing a MTO process which can convert the methanol stream 5001 to unpurified olefin stream 5002; an intermediate recovery system 5500 which can recover olefin stream 1 or 1*b* from stream 5002; the ethylene purification system 1000 or 2000 described hereinabove implementing the processes described hereinabove to yield polyethylene grade ethylene in purified ethylene stream 22; and a polyethylene polymerization system 6000 implementing a polymerization process which can convert purified ethylene stream 22 to polyethylene in stream 6001.

The gasification system 3000 can be any system implementing a process which converts coal to syngas known in the art with the aid of this disclosure. Gasification system 3000 can include a gasification reactor configured to gasify coal (e.g., solid, carbonaceous material) via reaction with oxygen, steam, or both oxygen and steam at appropriate conditions (e.g., greater than 932° F. (500° C.)) to produce syngas containing at least any one or a combination of carbon monoxide, hydrogen, and methane. The gasification reactor can utilize a fixed bed in counter-current or co-current configuration or a fluidized bed, for example. Examples of gasification systems and processes can be found in U.S. Pat. Nos. 2,876,660, 3,874,116, and 4,203,823, each of which is incorporated by reference in its entirety. The syngas flows in stream 4001 to methanol system 4000.

The methanol system 4000 can be any system implementing a process which converts syngas to methanol known in the art with the aid of this disclosure. The methanol system 4000 can include a syngas reactor having a catalyst therein which contacts the syngas obtained in stream 4001 under suitable conditions to yield methanol in stream 5001. An example of a methanol system and process can be found in U.S. Pat. No. 3,920,717, which is incorporated by reference in its entirety. An example of a system and process which converts coal to syngas and the syngas to methanol is found in U.S. Pat. No. 6,723,689, which is incorporated by reference in its entirety. The methanol flows in stream 5001 to the MTO system 5000.

MTO system 5000 can be any system implementing a process which converts methanol to olefins known in the art with the aid of this disclosure. MTO system 5000 can include a methanol-to-olefin reactor configured to convert methanol received from methanol system 4000 to olefins and yield the unpurified olefin stream 5002 and/or olefin stream 1 or 1*b*. In MTO system 5000, methanol can be contacted with a zeolite catalyst (e.g., aluminosilicate) under suitable temperature and pressure which yields an unpurified olefin stream 5002. Examples of MTO systems and processes can be found in U.S. Pat. Nos. 6,613,951 and 8,674,157, each of which is incorporated by reference in its entirety.

The unpurified olefin stream 5002 of MTO system 5000 can flow to an intermediate recovery system 5500 where ethylene in a concentration of at least 99 mol % can be recovered in olefin stream 1 or 1*b*. Alternatively, for an MTO system 5000 which can produce an effluent 5002 having at least 99 mol % ethylene, the unpurified olefin stream 5002 can be olefin stream 1 or 1*b* which can flow to the ethylene purification systems and processes (e.g., system 1000 or system 2000 and associated processes).

The intermediate recovery system 5500 can be any system implementing separations which recover ethylene in a concentration of at least 99 mol % to provide olefin stream 1 or 1*b*. The effluent of MTO system 5000 in stream 5002 can include, in addition to ethylene, other light olefins, diolefins, and light paraffins such as methane. Separations which remove these compounds such that at least 99 mol % ethylene is obtained in olefin stream 1 or 1*b* can include flashing, distillation, absorption, membrane separations, stripping, or a combination thereof. Examples of an intermediate recovery system 5500 and process are found in U.S. Pat. Nos. 4,499,327, 7,166,757, and 8,399,728, each of which is incorporated by reference in its entirety.

The effluent from the intermediate recovery system 5500 containing at least 99 mol % ethylene can flow in olefin stream 1 or 1*b* to one of the ethylene purification systems disclosed herein, e.g., system 1000 or system 2000. As described briefly above, MTO system 5000 can produce an effluent having at least 99 mol % ethylene without need for intermediate purification or recovery of ethylene. That is, the effluent of MTO system 5000 contains at least 99 mol % ethylene and therefore does not need to pass through intermediate recovery system 5500. Instead the on-spec effluent from the MTO system 5000 can flow as olefin stream 1 or 1*b* directly to an ethylene purification systems and processes, e.g., system 1000 or system 2000 (and associated processes), described herein.

System 1000 or 2000 as described herein provides an ethylene purification process to purify the olefin stream 1 or 1b received by said system 1000 or 2000 and yield purified ethylene stream 22 containing polyethylene grade ethylene according to the specifications described herein. Polyethylene grade ethylene flows in stream 22 from system 1000 or 2000 to a polymerization system 6000.

Polymerization system 6000 can be any system implementing a polyethylene polymerization process known in the art with the aid of this disclosure. The purified ethylene stream 22 can flow to one or more polymerization reactors, where the ethylene from the purified ethylene stream 22 is polymerized in the presence of a polymerization catalyst (e.g., chromium-based catalyst, Ziegler-Natta catalyst, or metallocene catalyst) and optionally a comonomer (e.g., 1-hexene) and/or hydrogen. Each of the one or more polymerization reactors can be a slurry loop reactor, a gas phase reactor, an autoclave reactor, a batch reactor, or a continuous-stirred tank reactor, for example. The polyethylene produced by polymerization system 6000 in stream 6001 can be a low density polyethylene (LDPE), a linear low density polyethylene (LLDPE), a medium density polyethylene (MDPE), a high density polyethylene (HDPE), or a combination thereof. Examples of polyethylene polymerization processes can be found in U.S. Pat. Nos. 3,248,179, 5,565,175, 5,575,979, 6,239,235, and 9,238,698, each of which is incorporated by reference in its entirety.

The systems and processes disclosed herein enable recovery of a high purity polyethylene process feed stream having 99.875 mol % ethylene from a feed olefin stream having at least 99 mol % ethylene and various contaminants at levels which deactivate and/or poison polymerization catalysts, by utilizing a specific order of contaminant removal, namely, removal of sulfur compounds followed by removal of acetylene, methyl acetylene, propadiene, and oxygen, followed by removal of carbon monoxide and hydrogen, followed by removal of polar contaminants.

In an embodiment, the purity of the high purity polyethylene process feed stream having 99.875 mol % ethylene can be measured using gas chromatography (GC) with flame ionization detection (FID) or thermal conductivity detection (TCD), or gas chromatography/mass spectrometry (GC/MS). An individual of ordinary skill in the art can identify other appropriate and effective methods of gas analysis; however, the preferred method is gas chromatography.

The disclosed systems and processes also provide different configurations for the sulfur guard bed (e.g., sulfur guard bed 100 of system 1000 or sulfur guard bed 150 of system 2000) depending on the sulfur compounds present in the olefin stream 1 or 1b recovered from a MTO process. A sulfur guard bed of desiccant can be used when the sulfur compounds in the olefin stream 1 or 1b do not include mercaptans, DMS, and DMDS (e.g., the sulfur compounds include/are $H_2S$ and COS). Alternatively, a sulfur guard bed of nickel catalyst can be used when additional or other sulfur compounds are present in the olefin stream 1 or 1b (e.g., mercaptans, DMS, and DMDS).

The disclosed systems and processes also enable energy conservation via use of cross flow heat exchangers to heat and cool various process streams. For example, system 1000 and its associated process(es) use cross flow heat exchangers 30 and 40 to facilitate heat exchange by utilizing the existing temperature differences between streams 1 or 1b and 18, and streams 7 and 13. Likewise, system 2000 and its associated process(es) use cross flow heat exchanger 45 to facilitate heat exchange by utilizing the existing temperature differences between streams 7 and 18. As a result of the use of cross flow heat exchangers, energy conservation, i.e., use of less energy, can be achieved, thus saving on operating costs.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

The data in the Examples below were generated through mass balance calculations understood by those with ordinary skill in the art. The manufacturers of the various catalysts, adsorbents, and desiccants used in the Examples provided information regarding the loading capacity of the different materials. For example, a material (e.g. catalyst, adsorbent, or desiccant) would be identified as having the capacity to adsorb a specific mass of a specific component per unit volume or unit mass of material. Using this information along with the stoichiometry of any chemical reactions taking place, the composition of the stream to be purified, and the desired composition of the purified stream, one can calculate how much material (e.g. catalyst, adsorbent, or desiccant) would be required to obtain the desired purity of the purified effluent stream.

Example 1

In Example 1 an ethylene purification system configured similar to system 1000 of FIG. 1 was designed to purify ethylene contained in an olefin stream obtained from a MTO process to yield a purified ethylene stream having 99.875 mol % ethylene.

The olefin stream contained ethylene, inerts, propylene, and contaminants (sulfur compounds of $H_2S$, COS, mercaptans, DMS, and DMDS; acetylene; methyl acetylene; propadiene; oxygen; hydrogen; carbon monoxide; carbon dioxide; water; alcohols; carbonyl compounds; phosphine; arsine; nitrous oxide; and ammonia). Phosphine, arsine, nitrous oxide, and ammonia were also contained in the olefin stream but at levels suitable for polyethylene grade ethylene.

The purification system was configured to remove the i) sulfur compounds in a first stage, ii) acetylene, methyl acetylene, propadiene, and oxygen in a second stage, iii) hydrogen and carbon monoxide in a third stage, and iv) carbon dioxide, water, alcohols, and carbonyl compounds in a fourth stage. That is, the olefin stream was first treated in a sulfur guard bed of nickel catalyst. The effluent of the sulfur guard bed was subsequently treated in an acetylene/oxygen converter. The effluent of the acetylene/oxygen converter was subsequently treated in a copper oxide bed, and the effluent of the copper oxide bed was subsequently treated in a polisher. Table 1 below shows the corresponding stream compositions:

TABLE 1

MTO Ethylene Purification Using Nickel Catalyst as the Sulfur Guard Bed

| Component | Units | Olefin Stream | Sulfur Guard Bed Effluent | Acetylene/ Oxygen Converter Effluent | Copper Oxide Bed Effluent | Ethylene Polisher Effluent |
|---|---|---|---|---|---|---|
| Ethylene | mol % (min) | 99.875 | 99.875 | 99.875 | 99.875 | 99.875 |
| Inerts | mol % (max) | 0.125 | 0.125 | 0.125 | 0.125 | 0.125 |
| Total Sulfur | ppm (mol) | 5 | 1 | 1 | 1 | 1 |

TABLE 1-continued

MTO Ethylene Purification Using Nickel
Catalyst as the Sulfur Guard Bed

| Component | Units | Olefin Stream | Sulfur Guard Bed Effluent | Acetylene/ Oxygen Converter Effluent | Copper Oxide Bed Effluent | Ethylene Polisher Effluent |
|---|---|---|---|---|---|---|
| Acetylene | ppm (mol) | 10 | 10 | 1 | 1 | 1 |
| Methyl Acetylene | ppm (mol) | 15 | 15 | 1 | 1 | 1 |
| Propadiene | ppm (mol) | 15 | 15 | 1 | 1 | 1 |
| Oxygen | ppm (mol) | 5 | 5 | 1 | 1 | 1 |
| Propylene | ppm (mol) | 20 | 20 | 50 | 50 | 50 |
| Hydrogen | ppm (mol) | 10 | 10 | 10 | 1 | 1 |
| Carbon Monoxide | ppm (mol) | 5 | 5 | 5 | 1 | 1 |
| Carbon Dioxide | ppm (mol) | 10 | 10 | 10 | 15 | 1 |
| Water | ppm (mol) | 10 | 10 | 20 | 30 | 1 |
| Total Alcohol | ppm (mol) | 10 | 10 | 10 | 10 | 1 |
| Total Carbonyl | ppm (mol) | 2 | 2 | 2 | 2 | 1 |
| Phosphine | ppm (mol) | 0.1 | 0.1 | 0.1 | 0.1 | 0.1 |
| Arsine | ppm (mol) | 0.1 | 0.1 | 0.1 | 0.1 | 0.1 |
| Nitrous Oxide | ppm (mol) | 1 | 1 | 1 | 1 | 1 |
| Ammonia | ppm (mol) | 1 | 1 | 1 | 1 | 1 |

As can be seen in Table 1, the olefin stream having 99.875 mol % ethylene and various other components (including contaminants) was successfully purified to remove the undesired components. The effluent of the polisher (i.e., the purified ethylene stream) contained 99.875 mol % ethylene and was polyethylene grade. The inerts in each of the streams in Table 1 included paraffins and nitrogen, where the paraffins are primarily methane, ethane and propane.

In the acetylene/oxygen converter, an additional 90 ppm (mol) hydrogen was added to enable the hydrogenation reactions to proceed to completion. As can be seen in Table 1, the hydrogen that was introduced in the acetylene/oxygen converter at a concentration of 90 ppm (mol) and introduced via the olefin stream at a concentration of 10 ppm (mol) was removed in the copper oxide bed to a level of 1 ppm (mol) in the copper oxide bed effluent. The design calculations for Example 1 assumed 90% conversion for the hydrogenation reactions in the acetylene/oxygen converter.

As can be seen in Table 1, the total sulfur content of the olefin stream was reduced in the sulfur guard bed, resulting in a concentration of 5 ppm (mol) total sulfur in the olefin stream and 1 ppm (mol) total sulfur in the sulfur guard bed effluent (as well as all effluents downstream of the sulfur guard bed).

The amounts of acetylene, methyl acetylene, propadiene, and oxygen were reduced in the acetylene/oxygen converter, indicated in Table 1 as i) a concentration of 10 ppm (mol) acetylene in the olefin stream and the sulfur guard bed effluent, and as 1 ppm (mol) acetylene in the acetylene/oxygen converter effluent (as well as all effluents downstream of the acetylene/oxygen converter), ii) a concentration of 15 ppm (mol) methyl acetylene and 15 ppm (mol) propadiene in the olefin stream and the sulfur guard bed effluent, and as 1 ppm (mol) methyl acetylene and as 1 ppm (mol) propadiene in the acetylene/oxygen converter effluent (as well as all effluents downstream of the acetylene/oxygen converter), and iii) a concentration of 5 ppm (mol) oxygen in the olefin stream and the sulfur guard bed effluent, and as 1 ppm (mol) oxygen in the acetylene/oxygen converter effluent (as well as all effluents downstream of the acetylene/oxygen converter).

The concentration of propylene in the system increased in the acetylene/oxygen converter, as indicated by a concentration of 20 ppm (mol) propylene in the olefin stream and sulfur guard bed effluent and by a concentration of 50 ppm (mol) propylene in the acetylene/oxygen converter effluent (as well as all effluents downstream of the acetylene/oxygen converter).

The amounts of hydrogen and carbon monoxide were reduced in the copper oxide bed, indicated in Table 1 as i) a concentration of 10 ppm (mol) hydrogen in the olefin stream, the sulfur guard bed effluent, and the acetylene/oxygen converter effluent, and as 1 ppm (mol) hydrogen in the copper oxide bed effluent (as well as all effluents downstream of the copper oxide bed), and ii) a concentration of 5 ppm (mol) carbon dioxide in the olefin stream, the sulfur guard bed effluent, and the acetylene/oxygen converter effluent, and as 1 ppm (mol) carbon monoxide in the copper oxide bed effluent (as well as all effluents downstream of the copper oxide bed).

Carbon dioxide was produced in the copper oxide catalyst bed, indicated in Table 1 by a concentration of carbon dioxide of 10 ppm (mol) in the olefin stream, the sulfur guard bed effluent, and the acetylene/oxygen converter effluent, and by a concentration of carbon dioxide of 15 ppm (mol) in the copper oxide bed effluent.

Water was produced in both the acetylene/oxygen converter and the copper oxide catalyst bed, indicated in Table 1 by i) a concentration of water of 10 ppm (mol) in the olefin stream and the sulfur guard bed effluent, ii) a concentration of water of 20 ppm (mol) in the acetylene/oxygen converter effluent, and iii) by a concentration of water of 30 ppm (mol) in the copper oxide bed effluent.

The concentrations of carbon dioxide, water, alcohols, and carbonyl compounds were reduced in the ethylene polisher containing desiccant, as indicated by i) a concentration of 15 ppm (mol) carbon dioxide in the copper oxide bed effluent, and a concentration of 1 ppm (mol) carbon dioxide in the polisher effluent, ii) a concentration of 30 ppm (mol) water in the copper oxide bed effluent, and a concentration of 1 ppm (mol) water in the polisher effluent, and ii) a concentration of 10 ppm (mol) alcohols in the copper oxide bed effluent, and a concentration of 1 ppm (mol) alcohols in the polisher effluent, and iv) a concentration of 2 ppm (mol) carbonyls in the copper oxide bed effluent, and a concentration of 1 ppm (mol) carbonyls in the polisher effluent.

Any changes in the concentration of phosphine and arsine were not detected beyond a sensitivity of 0.1 ppm (mol), as indicated by the concentration of said components as 0.1 ppm (mol) for all stream compositions in Table 1 of Example 1. Likewise, any changes in the concentration of nitrous oxide and ammonia were not detected beyond a sensitivity of 1 ppm (mol), as indicated by the concentration of said components as 1 ppm (mol) for all stream compositions in Table 1 of Example 1.

Example 2

In Example 2 an ethylene purification system configured similar to system 2000 of FIG. 2 was designed to purify ethylene contained in an olefin stream obtained from a MTO process to yield a purified ethylene stream having 99.875 mol % ethylene.

The olefin stream contained ethylene, inerts, propylene, and contaminants (sulfur compounds of $H_2S$ and COS; acetylene; methyl acetylene; propadiene; oxygen; hydrogen; carbon monoxide; carbon dioxide; water; alcohols; carbonyl compounds; phosphine; arsine; nitrous oxide; and ammonia). Phosphine, arsine, nitrous oxide, and ammonia were contained in the olefin stream at levels suitable for polyethylene grade ethylene.

The purification system was configured to remove the i) sulfur compounds, carbon dioxide, water, alcohols, and carbonyl compounds in a first stage, ii) acetylene, methyl acetylene, propadiene, and oxygen in a second stage, iii) hydrogen and carbon monoxide in a third stage, and iv) carbon dioxide, water, alcohols, and carbonyl compounds in a fourth stage. That is, the olefin stream was first treated in a sulfur guard bed of nickel catalyst. The effluent of the sulfur guard bed was subsequently treated in an acetylene/oxygen converter. The effluent of the acetylene/oxygen converter was subsequently treated in a copper oxide bed, and the effluent of the copper oxide bed was subsequently treated in a polisher. Table 2 below shows the corresponding stream compositions:

TABLE 2

MTO Ethylene Purification Using Desiccant as the Sulfur Guard Bed

| Component | Units | Olefin Stream | Sulfur Guard Bed Effluent | Acetylene/ Oxygen Converter Effluent | Copper Oxide Bed Effluent | Ethylene Polisher Effluent |
|---|---|---|---|---|---|---|
| Ethylene | mol % (min) | 99.875 | 99.875 | 99.875 | 99.875 | 99.875 |
| Inerts | mol % (max) | 0.125 | 0.125 | 0.125 | 0.125 | 0.125 |
| Total Sulfur | ppm (mol) | 5 | 1 | 1 | 1 | 1 |
| Acetylene | ppm (mol) | 10 | 10 | 1 | 1 | 1 |
| Methyl Acetylene | ppm (mol) | 15 | 15 | 1 | 1 | 1 |
| Propadiene | ppm (mol) | 15 | 15 | 1 | 1 | 1 |
| Oxygen | ppm (mol) | 5 | 5 | 1 | 1 | 1 |
| Propylene | ppm (mol) | 20 | 20 | 50 | 50 | 50 |
| Hydrogen | ppm (mol) | 10 | 10 | 10 | 1 | 1 |
| Carbon Monoxide | ppm (mol) | 5 | 5 | 5 | 1 | 1 |
| Carbon Dioxide | ppm (mol) | 10 | 1 | 1 | 5 | 1 |
| Water | ppm (mol) | 10 | 1 | 10 | 20 | 1 |
| Total Alcohol | ppm (mol) | 10 | 1 | 1 | 1 | 1 |
| Total Carbonyl | ppm (mol) | 2 | 1 | 1 | 1 | 1 |
| Phosphine | ppm (mol) | 0.1 | 0.1 | 0.1 | 0.1 | 0.1 |
| Arsine | ppm (mol) | 0.1 | 0.1 | 0.1 | 0.1 | 0.1 |
| Nitrous Oxide | ppm (mol) | 1 | 1 | 1 | 1 | 1 |
| Ammonia | ppm (mol) | 1 | 1 | 1 | 1 | 1 |

As can be seen in Table 2, the olefin stream having 99.875 mol % ethylene and various other components (including contaminants) was successfully purified to remove undesired components. The effluent of the polisher (i.e., the purified ethylene stream) contained 99.875 mol % ethylene and was polyethylene grade. The inerts in each of the streams in Table 1 included paraffins and nitrogen, where the paraffins are primarily methane, ethane and propane.

In the acetylene/oxygen converter, an additional 90 ppm (mol) hydrogen was added to enable the hydrogenation reactions to proceed to completion. As can be seen in Table 2, the hydrogen that was introduced in the acetylene/oxygen converter at a concentration of 90 ppm (mol) and via the olefin stream at a concentration of 10 ppm (mol) was removed in the copper oxide bed to a level of 1 ppm (mol) in the copper oxide bed effluent. The design calculations for Example 2 assumed 90% conversion for the hydrogenation reactions in the acetylene/oxygen converter.

As can be seen in Table 2, the total sulfur content of the olefin stream was reduced in the sulfur guard bed, indicated in Table 2 as a concentration of 5 ppm (mol) total sulfur in the olefin stream and 1 ppm (mol) total sulfur in the sulfur guard bed effluent (as well as all effluents downstream of the sulfur guard bed).

As a result of using desiccant in the sulfur guard bed, the amounts of carbon dioxide, water, alcohols, and carbonyl compounds were also reduced in the sulfur guard bed, indicated in Table 2 as i) a concentration of 10 ppm (mol) carbon dioxide in the olefin stream and a concentration of 1 ppm (mol) carbon dioxide in the sulfur guard bed effluent, ii) a concentration of 10 ppm (mol) water in the olefin stream and a concentration of 1 ppm (mol) water in the sulfur guard bed effluent, iii) a concentration of 10 ppm (mol) alcohols in the olefin stream and a concentration of 1 ppm (mol) alcohols in the sulfur guard bed effluent, and iv) a concentration of 2 ppm (mol) carbonyl compounds in the olefin stream and a concentration of 1 ppm (mol) carbonyl compounds in the sulfur guard bed effluent.

The amounts of acetylene, methyl acetylene, propadiene, and oxygen were reduced in the acetylene/oxygen converter, indicated in Table 2 as i) a concentration of 10 ppm (mol) acetylene in the olefin stream and the sulfur guard bed effluent, and as 1 ppm (mol) acetylene in the acetylene/oxygen converter effluent (as well as all effluents downstream of the acetylene/oxygen converter), ii) a concentration of 15 ppm (mol) methyl acetylene and 15 ppm (mol) propadiene in the olefin stream and the sulfur guard bed effluent, and as 1 ppm (mol) methyl acetylene and 1 ppm (mol) propadiene in the acetylene/oxygen converter effluent (as well as all effluents downstream of the acetylene/oxygen converter), and iii) a concentration of 5 ppm (mol) oxygen in the olefin stream and the sulfur guard bed effluent, and as 1 ppm (mol) oxygen in the acetylene/oxygen converter effluent (as well as all effluents downstream of the acetylene/oxygen converter).

The concentration of propylene in the system increased in the acetylene/oxygen converter, as indicated by a concentration of 20 ppm (mol) propylene in the olefin stream and sulfur guard bed effluent and by a concentration of 50 ppm (mol) propylene in the acetylene/oxygen converter effluent (as well as all effluents downstream of the acetylene/oxygen converter).

The amounts of hydrogen and carbon monoxide were reduced in the copper oxide bed, indicated in Table 2 as i) a concentration of 10 ppm (mol) hydrogen in the olefin stream, the sulfur guard bed effluent, and the acetylene/oxygen converter effluent, and as 1 ppm (mol) hydrogen in the copper oxide bed effluent (as well as all effluents downstream of the copper oxide bed), and ii) a concentration of 5 ppm (mol) carbon dioxide in the olefin stream, the sulfur guard bed effluent, and the acetylene/oxygen converter effluent, and as 1 ppm (mol) carbon monoxide in the copper oxide bed effluent (as well as all effluents downstream of the copper oxide bed).

Carbon dioxide was produced in the copper oxide catalyst bed, indicated in Table 2 by a concentration of carbon dioxide of 1 ppm (mol) in the acetylene/oxygen converter effluent, and by a concentration of carbon dioxide of 5 ppm (mol) in the copper oxide bed effluent.

Water was produced in both the acetylene/oxygen converter and the copper oxide catalyst bed, indicated in Table 2 by i) a concentration of water of 1 ppm (mol) in the sulfur guard bed effluent, ii) a concentration of water of 10 ppm (mol) in the acetylene/oxygen converter effluent, and iii) by a concentration of water of 20 ppm (mol) in the copper oxide bed effluent.

The concentrations of carbon dioxide and water were reduced in the ethylene polisher containing desiccant, as indicated by i) a concentration of 5 ppm (mol) carbon dioxide in the copper oxide bed effluent, and a concentration of 1 ppm (mol) carbon dioxide in the polisher effluent, and ii) a concentration of 20 ppm (mol) water in the copper oxide bed effluent, and a concentration of 1 ppm (mol) water in the polisher effluent.

As discussed above, the sulfur guard bed of Example 2 contained a desiccant; thus, the sulfur guard bed removed alcohols and carbonyls upstream of the polisher. Any removal of alcohols and carbonyls by the desiccant of the polisher was undetected in Example 2 beyond the concentration of 1 ppm (mol) for each of alcohols and carbonyl compounds which entered the polisher.

Any changes in the concentration of phosphine and arsine were not detected beyond a sensitivity of 0.1 ppm (mol), as indicated by the concentration of said components as 0.1 ppm (mol) for all stream compositions in Table 2 of Example 2. Likewise, any changes in the concentration of nitrous oxide and ammonia were not detected beyond a sensitivity of 1 ppm (mol), as indicated by the concentration of said components as 1 ppm (mol) for all stream compositions in Table 2 of Example 2.

Additional Disclosure

The following is provided as additional disclosure for combinations of features and aspects of the present invention.

Aspect 1 is a process for purifying an olefin stream comprising at least 99 mol % ethylene, wherein the process comprises:

(a) passing the olefin stream through a sulfur guard bed to remove sulfur compounds and to yield a substantially sulfur-free effluent;

(b) contacting the substantially sulfur-free effluent from (a) with a hydrogenation catalyst to yield a substantially sulfur-, oxygen-, acetylene-, methyl acetylene-, and propadiene-free effluent;

(c) passing the substantially sulfur-, oxygen-, acetylene-, methyl acetylene-, and propadiene-free effluent from (b) through a copper-metal containing catalyst bed to remove carbon monoxide and hydrogen and to yield a substantially sulfur-, oxygen-, acetylene-, methyl acetylene-, propadiene-, carbon monoxide-, and hydrogen-free effluent; and (d) passing the substantially sulfur-, oxygen-, acetylene-, methyl acetylene-, propadiene-, carbon monoxide-, and hydrogen-free effluent from (c) through a desiccant comprising alumina, molecular sieve, or a hybrid alumina-zeolite composite to remove polar contaminants and yield a purified ethylene stream comprising greater than or equal to 99.875 mol % ethylene.

Aspect 2 is the process of aspect 1, wherein the purified ethylene stream from (d) comprises equal to or less than 1 ppm (mol) of acetylene, equal to or less than 5 ppm (mol) hydrogen, equal to or less than 1 ppm (mol) carbon monoxide, equal to or less than 1 ppm (mol) water, and equal to or less than 1 ppm (mol) total sulfur.

Aspect 3 is the process of any one of aspects 1-2, further comprising:
  converting coal to syngas;
  converting syngas to methanol; and
  converting methanol to olefins to yield the olefin stream.

Aspect 4 is the process of any one of aspects 1-3, further comprising a step of:
  feeding the purified ethylene stream to one or more polymerization reactors.

Aspect 5 is the process of any one of aspects 1-4, further comprising:
  heating the olefin stream by transferring thermal energy from the substantially sulfur-, oxygen-, acetylene-, methyl acetylene-, propadiene-, carbon monoxide-, and hydrogen-free effluent to the olefin stream in a first heat exchanger prior to (a); and
  cooling the substantially sulfur-free effluent by transferring thermal energy to the substantially sulfur-, oxygen-, acetylene-, methyl acetylene-, and propadiene-free effluent from the substantially sulfur-free effluent inside a second heat exchanger prior to (b).

Aspect 6 is the process of any one of aspects 1-5, further comprising:
  cooling the substantially sulfur-free effluent by transferring thermal energy to the substantially sulfur-, oxygen-, acetylene-, methyl acetylene-, propadiene-, carbon monoxide-, and hydrogen-free effluent from the substantially sulfur-free effluent inside a heat exchanger prior to (b).

Aspect 7 is the process as described in any one of aspects 1-6, further comprising:
  introducing hydrogen into or upstream of an acetylene/oxygen converter which contains the hydrogenation catalyst.

Aspect 8 is the process of aspect 7, further comprising:
  converting at least a portion of the introduced hydrogen to water in the copper-metal containing catalyst bed.

Aspect 9 is the process of any one of aspects 1-8, wherein the sulfur guard bed comprises a nickel catalyst.

Aspect 10 is the process of any one of aspects 1-8, wherein the sulfur guard bed comprises a second desiccant comprising alumina, molecular sieve, or a hybrid alumina-zeolite composite.

Aspect 11 is the process of any one of aspects 1-10, wherein the hydrogenation catalyst comprises palladium.

Aspect 12 is the process of any one of aspects 1-11, further comprising:
  regenerating one or more of the sulfur guard bed, the copper-metal containing catalyst bed, and the desiccant with a regenerating gas selected from nitrogen, sulfur-free methane, sulfur-free ethane, sulfur-free propane, sulfur-free butanes, nobles gases, or a combination thereof.

Aspect 13 is the process of any one of aspects 1-12, wherein the polar contaminants removed in (d) include water generated in (b) by the conversion of oxygen to water.

Aspect 14 is the process of any one of aspects 1-13, wherein the polar contaminants removed in (d) include water generated in (c) by the conversion of hydrogen to water.

Aspect 15 is a system for purifying an olefin stream comprising at least 99 mol % ethylene, wherein the system comprises:

a sulfur guard bed configured to remove sulfur compounds from the olefin stream to yield a substantially sulfur-free effluent;

an acetylene/oxygen converter configured to contact the substantially sulfur-free effluent with a hydrogenation catalyst to yield a substantially sulfur-, oxygen-, acetylene-, methyl acetylene-, and propadiene-free effluent;

a copper-metal containing catalyst bed configured to remove carbon monoxide and hydrogen from the substantially sulfur-, oxygen-, acetylene-, methyl acetylene-, and propadiene-free effluent to yield a substantially sulfur-, oxygen-, acetylene-, methyl acetylene-, propadiene-, carbon monoxide-, and hydrogen-free effluent; and a polisher configured to remove polar contaminants from the substantially sulfur-, oxygen-, acetylene-, methyl acetylene-, propadiene-, carbon monoxide-, and hydrogen-free effluent to yield a purified ethylene stream comprising 99.875 mol % or more ethylene, equal to or less than 1 ppm (mol) of acetylene, equal to or less than 5 ppm (mol) hydrogen, equal to or less than 1 ppm (mol) carbon monoxide, equal to or less than 1 ppm (mol) water, and equal to or less than 1 ppm (mol) total sulfur.

Aspect 16 is the system of aspect 15, further comprising:

a gasification system configured to convert coal to syngas;

a methanol system configured to convert syngas to methanol; and a methanol-to-olefin system configured to convert methanol received from the methanol system to olefins.

Aspect 17 is the system of any one of aspects 15-16, further comprising:

one or more polymerization reactors configured to receive the purified ethylene stream and polymerize ethylene to yield a polyethylene.

Aspect 18 is the system of any one of aspects 15-17, further comprising:

a first heat exchanger to heat the olefin stream by exchanging thermal energy with the substantially sulfur-, oxygen-, acetylene-, methyl acetylene-, propadiene-, carbon monoxide-, and hydrogen-free effluent; and a second heat exchanger to cool the substantially sulfur-free effluent by exchanging thermal energy with the substantially sulfur-, oxygen-, acetylene-, methyl acetylene-, and propadiene-free effluent.

Aspect 19 is the system of any one of aspects 15-17, further comprising:

a heat exchanger to heat the substantially sulfur-free effluent by exchanging thermal energy with the substantially sulfur-, oxygen-, acetylene-, methyl acetylene-, propadiene-, carbon monoxide-, and hydrogen-free effluent.

Aspect 20 is the system of any one of aspects 15-19, wherein the polar contaminants removed in the polisher include water generated in the acetylene/oxygen converter, the copper-metal containing catalyst bed, or both the acetylene/oxygen converter and the copper-metal containing catalyst bed.

Aspect 21 is the system of any one of aspects 15-20, wherein the polar contaminants include one or more of water, ammonia, alcohols, and oxygenates.

Aspect 22 is the system of any one of aspects 15-21, wherein the copper-metal containing catalyst bed is a copper-metal containing catalyst bed.

Aspect 23 is the system of aspect 22, where the copper oxide is Cu(II)O.

Aspect 24 is the system of aspects 15-23, wherein the polisher is configured to remove light acid gases, carbon dioxide and carbonyl sulfide from the substantially sulfur-, oxygen-, acetylene-, methyl acetylene-, propadiene-, carbon monoxide-, and hydrogen-free effluent to yield the purified ethylene stream.

While aspects and embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, 5, 6, . . . ; greater than 0.10 includes 0.11, 0.12, 0.13, 0.14, 0.15, . . . ). For example, whenever a numerical range with a lower limit, $R_l$, and an upper limit, $R_u$, is disclosed, any number falling within the range is specifically disclosed. In particular, the following numbers within the range are specifically disclosed: $R=R_l+k^* (R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention.

What is claimed is:

1. A process for purifying an olefin stream comprising at least 99 mol % ethylene, wherein the process comprises:

(a) passing the olefin stream through a sulfur guard bed to remove sulfur compounds and to yield a substantially sulfur-free effluent;

(b) contacting the substantially sulfur-free effluent from (a) with a hydrogenation catalyst to yield a substantially sulfur-, oxygen-, acetylene-, methyl acetylene-, and propadiene-free effluent;

(c) passing the substantially sulfur-, oxygen-, acetylene-, methyl acetylene-, and propadiene-free effluent from (b) through a copper-metal containing catalyst bed to remove carbon monoxide and hydrogen and to yield a substantially sulfur-, oxygen-, acetylene-, methyl acetylene-, propadiene-, carbon monoxide-, and hydrogen-free effluent; and (d) passing the substantially sulfur-, oxygen-, acetylene-, methyl acetylene-, propadiene-, carbon monoxide-, and hydrogen-free effluent from (c) through a desiccant comprising alumina, molecular sieve, or a hybrid alumina-zeolite composite to remove polar contaminants and yield a purified ethylene stream comprising greater than or equal to 99.875 mol % ethylene.

2. The process of claim 1, wherein the purified ethylene stream from (d) comprises equal to or less than 1 ppm (mol) of acetylene, equal to or less than 5 ppm (mol) hydrogen, equal to or less than 1 ppm (mol) carbon monoxide, equal to or less than 1 ppm (mol) water, and equal to or less than 1 ppm (mol) total sulfur.

3. The process of claim 1, further comprising:
converting coal to syngas;
converting syngas to methanol; and
converting methanol to olefins to yield the olefin stream.

4. The process of claim 1, further comprising a step of:
feeding the purified ethylene stream to one or more polymerization reactors.

5. The process of claim 1, further comprising:
heating the olefin stream by transferring thermal energy from the substantially sulfur-oxygen-, acetylene-, methyl acetylene-, propadiene-, carbon monoxide-, and hydrogen-free effluent to the olefin stream in a first heat exchanger prior to (a); and
cooling the substantially sulfur-free effluent by transferring thermal energy to the substantially sulfur-, oxygen-, acetylene-, methyl acetylene-, and propadiene-free effluent from the substantially sulfur-free effluent inside a second heat exchanger prior to (b).

6. The process of claim 1, further comprising:
cooling the substantially sulfur-free effluent by transferring thermal energy to the substantially sulfur-, oxygen-, acetylene-, methyl acetylene-, propadiene-, carbon monoxide-, and hydrogen-free effluent from the substantially sulfur-free effluent inside a heat exchanger prior to (b).

7. The process as described in claim 1, further comprising:
introducing hydrogen into or upstream of an acetylene/oxygen converter which contains the hydrogenation catalyst.

8. The process of claim 7, further comprising:
converting at least a portion of the introduced hydrogen to water in the copper-metal containing catalyst bed.

9. The process of claim 1, wherein the sulfur guard bed comprises a nickel catalyst.

10. The process of claim 1, wherein the sulfur guard bed comprises a second desiccant comprising alumina, molecular sieve, or a hybrid alumina-zeolite composite.

11. The process of claim 1, wherein the hydrogenation catalyst comprises palladium.

12. The process of claim 1, further comprising:
regenerating one or more of the sulfur guard bed, the copper-metal containing catalyst bed, and the desiccant with a regenerating gas selected from nitrogen, sulfur-free methane, sulfur-free ethane, sulfur-free propane, sulfur-free butanes, nobles gases, or a combination thereof.

13. The process of claim 1, wherein the polar contaminants removed in (d) include water generated in (b) by the conversion of oxygen to water.

14. The process of claim 13, wherein the polar contaminants removed in (d) include water generated in (c) by the conversion of hydrogen to water.

15. A system for purifying an olefin stream comprising at least 99 mol % ethylene, wherein the system comprises:
a sulfur guard bed configured to remove sulfur compounds from the olefin stream to yield a substantially sulfur-free effluent;
an acetylene/oxygen converter configured to contact the substantially sulfur-free effluent with a hydrogenation catalyst to yield a substantially sulfur-, oxygen-, acetylene-, methyl acetylene-, and propadiene-free effluent;
a copper-metal containing catalyst bed configured to remove carbon monoxide and hydrogen from the substantially sulfur-, oxygen-, acetylene-, methyl acetylene-, and propadiene-free effluent to yield a substantially sulfur-, oxygen-, acetylene-, methyl acetylene-, propadiene-carbon monoxide-, and hydrogen-free effluent; and
a polisher configured to remove polar contaminants from the substantially sulfur-, oxygen-, acetylene-, methyl acetylene-, propadiene-, carbon monoxide-, and hydrogen-free effluent to yield a purified ethylene stream comprising 99.875 mol % or more ethylene, equal to or less than 1 ppm (mol) of acetylene, equal to or less than 5 ppm (mol) hydrogen, equal to or less than 1 ppm (mol) carbon monoxide, equal to or less than 1 ppm (mol) water, and equal to or less than 1 ppm (mol) total sulfur.

16. The system of claim 15, further comprising:
a gasification system configured to convert coal to syngas;
a methanol system configured to convert syngas to methanol; and
a methanol-to-olefin system configured to convert methanol received from the methanol system to olefins.

17. The system of claim 15, further comprising:
one or more polymerization reactors configured to receive the purified ethylene stream and polymerize ethylene to yield a polyethylene.

18. The system of claim 15, further comprising:
a first heat exchanger to heat the olefin stream by exchanging thermal energy with the substantially sulfur-, oxygen-, acetylene-, methyl acetylene-, propadiene-, carbon monoxide-, and hydrogen-free effluent; and
a second heat exchanger to cool the substantially sulfur-free effluent by exchanging thermal energy with the substantially sulfur-, oxygen-, acetylene-, methyl acetylene-, and propadiene-free effluent.

19. The system of claim 15, further comprising:
a heat exchanger to heat the substantially sulfur-free effluent by exchanging thermal energy with the substantially sulfur-, oxygen-, acetylene-, methyl acetylene-, propadiene-, carbon monoxide-, and hydrogen-free effluent.

20. The system of claim 15, wherein the polar contaminants removed in the polisher include water generated in the acetylene/oxygen converter, the copper-metal containing catalyst bed, or both the acetylene/oxygen converter and the copper-metal containing catalyst bed.

21. The system of claim 15, wherein the polar contaminants include one or more of water, ammonia, alcohols, and oxygenates.

22. The system of claim 15, wherein the copper-metal containing catalyst bed is a copper oxide containing catalyst bed.

23. The system of claim 22, where the copper oxide is Cu(II)O.

24. The system of claim 15, wherein the polisher is configured to remove light acid gases, carbon dioxide and carbonyl sulfide from the substantially sulfur-, oxygen-, acetylene-, methyl acetylene-, propadiene-, carbon monoxide-, and hydrogen-free effluent to yield the purified ethylene stream.

\* \* \* \* \*